US006689133B2

(12) United States Patent
Morrison et al.

(10) Patent No.: US 6,689,133 B2
(45) Date of Patent: *Feb. 10, 2004

(54) MULTI-AXIAL BONE ANCHOR SYSTEM

(75) Inventors: Matthew M. Morrison, Cordova, TN (US); B. Thomas Barker, Memphis, TN (US); John Stewart Young, Memphis, TN (US); Jeffrey W. Beale, Arlington, TN (US); Chris E. Johnson, Germantown, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/978,932

(22) Filed: Oct. 16, 2001

(65) Prior Publication Data

US 2002/0026194 A1 Feb. 28, 2002

Related U.S. Application Data

(63) Continuation of application No. 09/526,188, filed on Mar. 15, 2000, now Pat. No. 6,315,779.
(60) Provisional application No. 60/129,587, filed on Apr. 16, 1999, and provisional application No. 60/149,774, filed on Aug. 19, 1999.

(51) Int. Cl.$^7$ .............................................. A61B 17/80
(52) U.S. Cl. ........................................ 606/71; 606/72
(58) Field of Search ............................. 606/69–71, 86, 606/105, 72, 73, 60, 61; 411/432, 433, 1–5, 531, 533

(56) References Cited

U.S. PATENT DOCUMENTS

| 3,191,486 A | * | 6/1965 | Gibbens ........................ 411/4 |
| 4,627,774 A | * | 12/1986 | Bradley ........................ 411/5 |
| 4,717,299 A | * | 1/1988 | Underwood ................. 411/11 |
| 4,729,703 A | * | 3/1988 | Sato ............................ 411/5 |
| 5,108,395 A | | 4/1992 | Laurain |
| 5,129,899 A | | 7/1992 | Small et al. |
| 5,154,560 A | * | 10/1992 | Copito ...................... 411/266 |
| 5,190,423 A | * | 3/1993 | Ewing ....................... 411/134 |
| 5,234,431 A | | 8/1993 | Keller |
| 5,261,910 A | | 11/1993 | Warden et al. |
| 5,290,288 A | | 3/1994 | Vignaud et al. |

(List continued on next page.)

FOREIGN PATENT DOCUMENTS

| DE | 197 20 782 A1 | 11/1998 |
| FR | 2 758 971 | 8/1998 |
| FR | 2 763 828 | 12/1998 |

Primary Examiner—Kevin Shaver
Assistant Examiner—Michael B. Priddy
(74) Attorney, Agent, or Firm—Woodard, Emhardt, Moriarty, McNett & Henry LLP

(57) ABSTRACT

A multi-axial bone fixation implant includes an elongated member, one or more bone anchor assemblies, and stabilizer members which are fitted within the elongated member. A bone bolt having cancellous threads on one end and machine threads at the opposing end and an enlarged portion between these sections is also provided. The bone bolt is anchored into a bone via the cancellous thread end. The machine threaded end passes through an opening of the elongated member and the stabilizer, and is engaged by a coupled washer and nut. The washer includes an undercut within its oblong aperture, and the nut includes a projecting sleeve. The sleeve is inserted into the washer aperture and expanded, so that the undercut retains the sleeve within the washer without impairing the rotatability or translatability of the nut and washer with respect to each other. When locked by the nut and washer atop the elongated member, the enlarged portion of the bolt is forced against an inside wall of the stabilizer, which is in turn locked against the elongated member. Accordingly, the elongated member is fixed with respect to the bone anchor at one of an infinite number of multi-axial angles.

39 Claims, 10 Drawing Sheets

U.S. PATENT DOCUMENTS

| | | | |
|---|---|---|---|
| 5,304,179 A | | 4/1994 | Wagner |
| 5,330,477 A | | 7/1994 | Crook |
| 5,344,421 A | | 9/1994 | Crook |
| 5,346,493 A | | 9/1994 | Stahurski et al. |
| 5,380,325 A | * | 1/1995 | Lahille et al. .................. 606/61 |
| 5,380,326 A | | 1/1995 | Lin |
| 5,439,463 A | | 8/1995 | Lin |
| 5,486,176 A | | 1/1996 | Hildebrand et al. |
| 5,520,688 A | | 5/1996 | Lin |
| 5,527,315 A | | 6/1996 | Jeanson et al. |
| 5,531,747 A | | 7/1996 | Ray |
| 5,582,496 A | * | 12/1996 | Ambrico et al. ............. 411/432 |
| 5,584,626 A | * | 12/1996 | Assmundson .................. 411/6 |
| 5,591,166 A | | 1/1997 | Bernhardt et al. |
| 5,601,553 A | | 2/1997 | Trebing et al. |
| 5,603,713 A | | 2/1997 | Aust et al. |
| 5,613,967 A | | 3/1997 | Engelhardt et al. |
| 5,613,968 A | | 3/1997 | Lin |
| 5,616,142 A | | 4/1997 | Yuan et al. |
| 5,620,443 A | * | 4/1997 | Gertzbein et al. ............. 606/61 |
| 5,665,089 A | | 9/1997 | Dall et al. |
| 5,676,666 A | * | 10/1997 | Oxland et al. ................. 606/61 |
| 5,728,127 A | | 3/1998 | Asher et al. |
| 5,735,853 A | | 4/1998 | Olerud |
| 5,797,912 A | | 8/1998 | Runciman et al. |
| 5,810,823 A | | 9/1998 | Klaue et al. |
| 5,885,286 A | | 3/1999 | Sherman et al. |
| 5,984,923 A | | 11/1999 | Breard |
| 5,984,924 A | | 11/1999 | Asher et al. |
| 6,039,738 A | | 3/2000 | Sanders et al. |
| 6,136,002 A | | 10/2000 | Shih et al. |
| 6,159,213 A | | 12/2000 | Rogozinski |
| 6,220,801 B1 | * | 4/2001 | Lin .............................. 411/9 |
| 6,224,602 B1 | | 5/2001 | Hayes |
| 6,248,105 B1 | | 6/2001 | Schläpfer et al. |

* cited by examiner

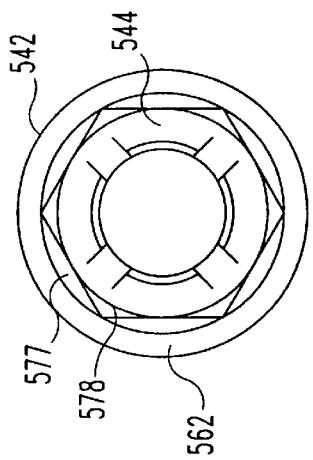
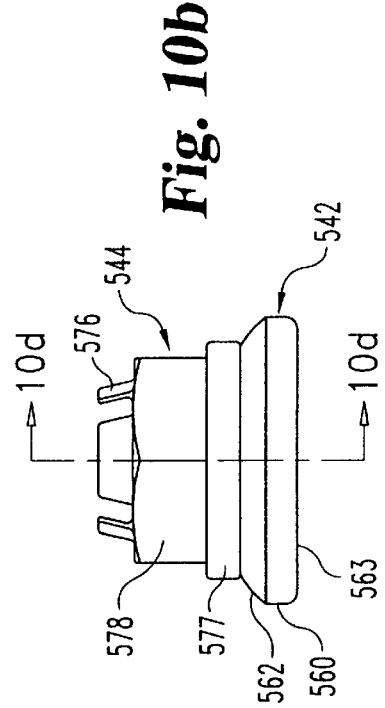
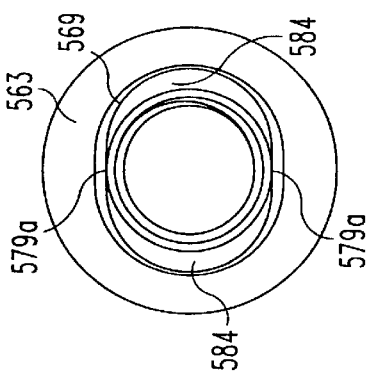
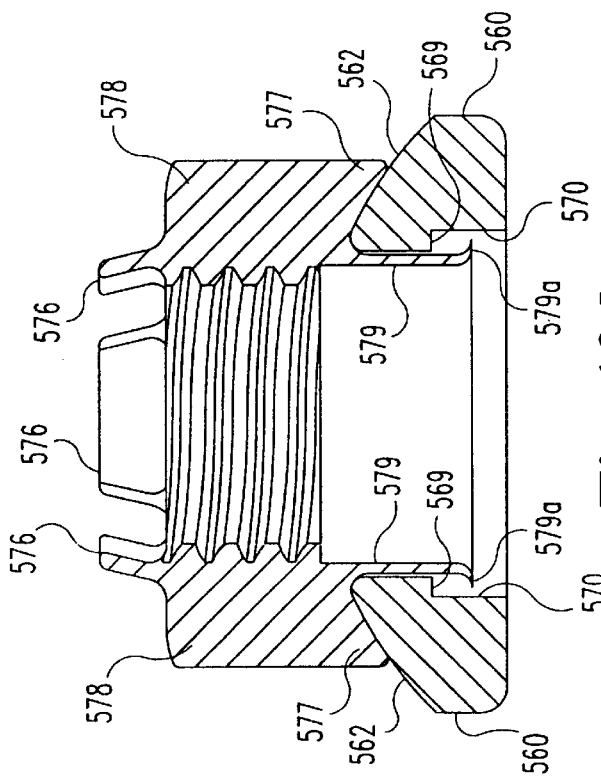

MULTI-AXIAL BONE ANCHOR SYSTEM

This application is a continuation of U.S. application Ser. No. 09/526,188, filed Mar. 5, 2000, now U.S. Pat. No. 6,315,779, which claimed the benefit of U.S. Provisional Application Serial No. 60/129,587, filed Apr. 16, 1999, and No. 60/149,774, filed Aug. 19, 1999, and this application claims the benefits thereof under 35 U.S.C. 119(e) and 120.

FIELD OF THE INVENTION

The present invention relates to an orthopedic implant assembly for use in stabilizing bone members in a desired spatial relationship and correcting bone mis-alignment disorders. In particular, the invention concerns a multi-axial spinal fixation system incorporating an elongated member such as a plate.

BACKGROUND OF THE INVENTION

In the art of orthopedic surgery, and particularly in spinal surgery, it has long been known to affix an elongated member, such as a plate or rod, to bones in order to hold them and support them in a given position. For example, in a procedure to fuse damaged, diseased, malformed or otherwise abnormal vertebrae, the vertebrae are positioned in a corrected position by a surgeon. An elongated plate is placed adjacent to the vertebral bone, and bone anchors, such as specially-configured screws or bolts, are employed to secure the plate to the bones. With such anchors placement is accomplished by drilling one or more holes in the bone(s), and threading the anchors into the holes. As examples, see U.S. Pat. No. 5,676,666 to Oxland et al., U.S. Pat. No. 5,613,967 to Engelhardt et al., and U.S. Pat. No. 5,603,713 to Aust et al. An anchor can be connected to the bone, as by threading into a vertebral hole, through a plate, or alternatively the plate can be placed in position over or around the anchor after the anchor is connected to the bone. The anchor and plate are then secured to each other to minimize or prevent relative movement. In this way, bones may be spinal held and/or supported in proper alignment for healing.

It has been found desirable for implant systems to have the capability for angular orientation of a bolt or other anchor in multiple planes relative to the elongated member or other fixation mechanisms of the implant system. Such features enable bone anchors to be placed at angles which are optimal for anchoring, thus reducing the chance of loosening, pull-out or other movement of the anchors while not compromising the optimal positioning of the fixation plate. Additionally, such systems alleviate awkwardness frequently found in spinal surgery due to uneven bone surfaces and the abnormality to be corrected and generally require less adjustment to the implant, rendering corrective surgery easier for the surgeon and less traumatic for the patient.

Various approaches have been used to achieve such multi-axial capability. For example, U.S. Pat. No. 5,735,853 to Olerud discloses an implant device in which a bone bolt can occupy different angular positions in relation to a plate by providing a compressible spherical collar which snap-fits around the bolt, which collar is rotatable and tiltable in a spherical opening in a plate insert. The compression fit of the bolt and collar within the plate can present difficulty in assembling the apparatus, particularly in a fluid-prevalent environment.

Another approach is shown in U.S. Pat. No. 5,304,179 to Wagner, which shows a bone screw fixed inside a bushing at an angle with respect to the longitudinal axis of the bushing. The bushing is rotatable within a portion of a connector angled with respect to the axis of the adjoining rod-based instrumentation. The connector is rotatable around the instrumentation axis. The Wagner system permits only discrete positions of a bone screw in three-dimensional space to be achieved, and the bushings add extra length and profile to the construct, as well as extra parts for the surgeon to handle and arrange.

A third approach is shown in U.S. Pat. No. 5,984,924 to Asher et. al., which shows a bone alignment system having an elongated bone alignment member sandwiched between two pairs of washers. Each such pair of washers have corresponding surfaces that mate together in a "ball and socket" configuration to potentially occupy a plurality of positions. When the shaft of a bone anchor extends through each washer pair, and also through an aperture of the elongated member, the washer pairs enable the shaft to be oriented at various angles relative to the elongated member. This approach also requires a plurality of small parts for handling and assembly during surgery. Further, since the washers in that system lie outside of the elongated member, they increase the thickness of the overall construct, with the attendant increase in the difficulty of use in a small surgical space and in the potential for patient discomfort.

There is therefore a need remaining in the art for a multi-axial bone anchor system which minimizes the number of parts used to engage a bone anchor to an elongated member such as a spinal plate in various angular orientations. There is also a need for a lower-profile, smaller-dimensioned multi-axial bone anchor that allows the positioning of the bone anchor to be adjustable through a continuous range of spatial angles and linear positions with respect to the elongated member.

SUMMARY OF THE INVENTION

The present invention provides, in one embodiment, an orthopedic implant system including a plate member for placement adjacent and along one or more bones, such as vertebrae, and having a longitudinal axis. The plate member includes at least one slot substantially parallel to the plate axis, which slot includes a channel portion that extends through substantially the entire longitudinal dimension of the plate member. Also provided is a stabilizer including an opening therethrough substantially bounded by a wall, the opening having a longitudinal axis and the stabilizer further including at least one finger portion extending laterally with respect to the opening axis, wherein said finger portion is received within the plate channel so that the stabilizer opening communicates with the plate slot. A bone bolt having a bone engaging portion, an intermediate portion and a threaded post portion extends through the stabilizer opening and the plate slot so that the bolt's intermediate portion is adjacent the wall of the stabilizer. Additionally, a washer having a rounded top surface, a bottom surface, and an aperture therethrough adapted for fitting around a portion of the bolt, as well as a nut separate from the washer and having a body portion, a skirt portion, a threaded hole extending through the body portion for threaded engagement with the bolt are provided, and the nut and the washer are coupled together prior to engagement with the bolt.

The nut and the washer may be rotatable with respect to each other and translatable with respect to each other. The nut may include a sleeve portion partially within the nut's skirt portion and substantially concentric with the nut's hole. Additionally, the washer can include an undercut having a first diameter within the washer's aperture, and the nut and the washer are coupled together by inserting the sleeve portion into the aperture and expanding a part of the sleeve portion, which may be an end of the sleeve portion, to a second diameter greater than the diameter of the undercut. The expansion can be caused by swaging, flaring, or other processes.

Other features, advantages and objects will be evident from the following specification.

BRIEF DESCRIPTION OF THE DRAWINGS

FIG. 4b is a side elevational view of the embodiment of the orthopedic plate illustrated in FIG. 4a.

FIG. 8b is a bottom view of the embodiment of the washer illustrated in FIG. 8a.

FIG. 9b is a top view of the embodiment of the nut illustrated in FIG. 9a.

FIG. 10a is a top view of one embodiment of the washer-nut combination used in the embodiment of the invention illustrated in FIG. 2.

FIG. 10b is a side elevational view of the embodiment of the washer-nut combination illustrated in FIG. 10a.

FIG. 10c is a bottom view of the embodiment of the washer-nut combination illustrated in FIG. 10a.

FIG. 10d is a cross-sectional view of the embodiment of the washer-nut combination illustrated in FIG. 10a, taken along line 10d—10d in FIG. 10b and viewed in the direction of the arrows.

DESCRIPTION OF THE PREFERRED EMBODIMENT

Figure 1:
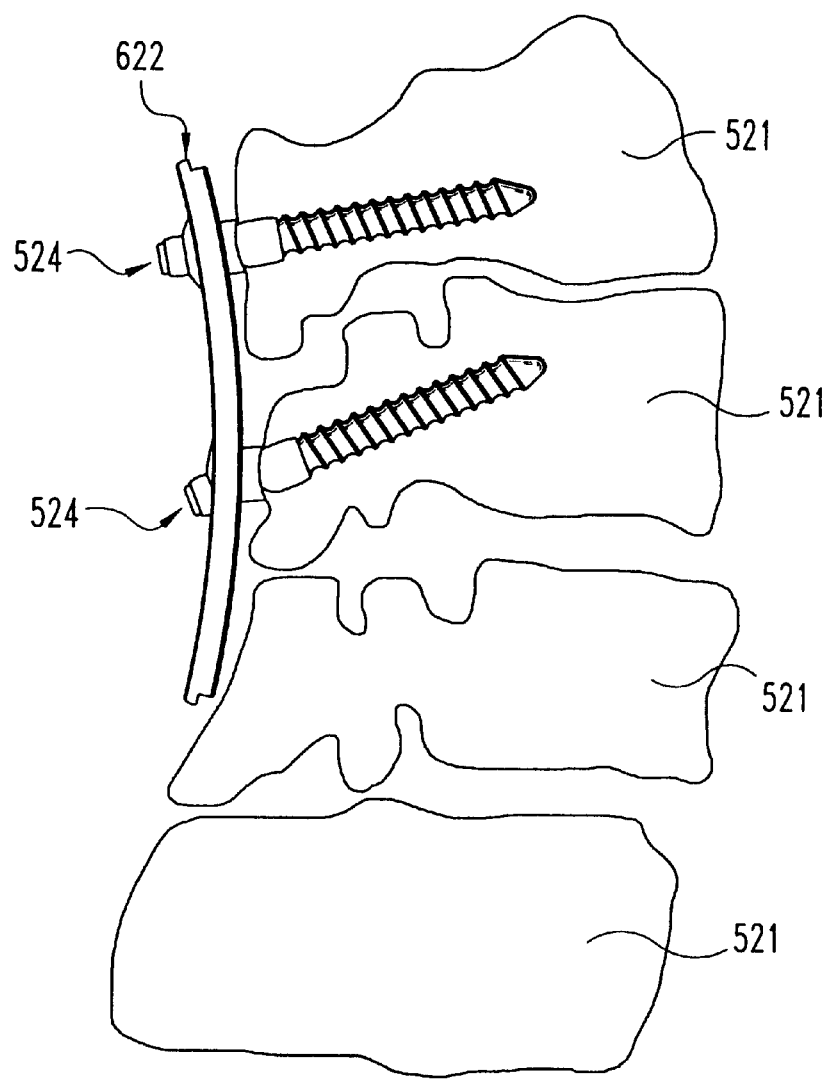
FIG. 1 is a schematic drawing illustrating an embodiment of the orthopedic implant of the present invention, implanted in vertebrae.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates are also included.

Figure 2:
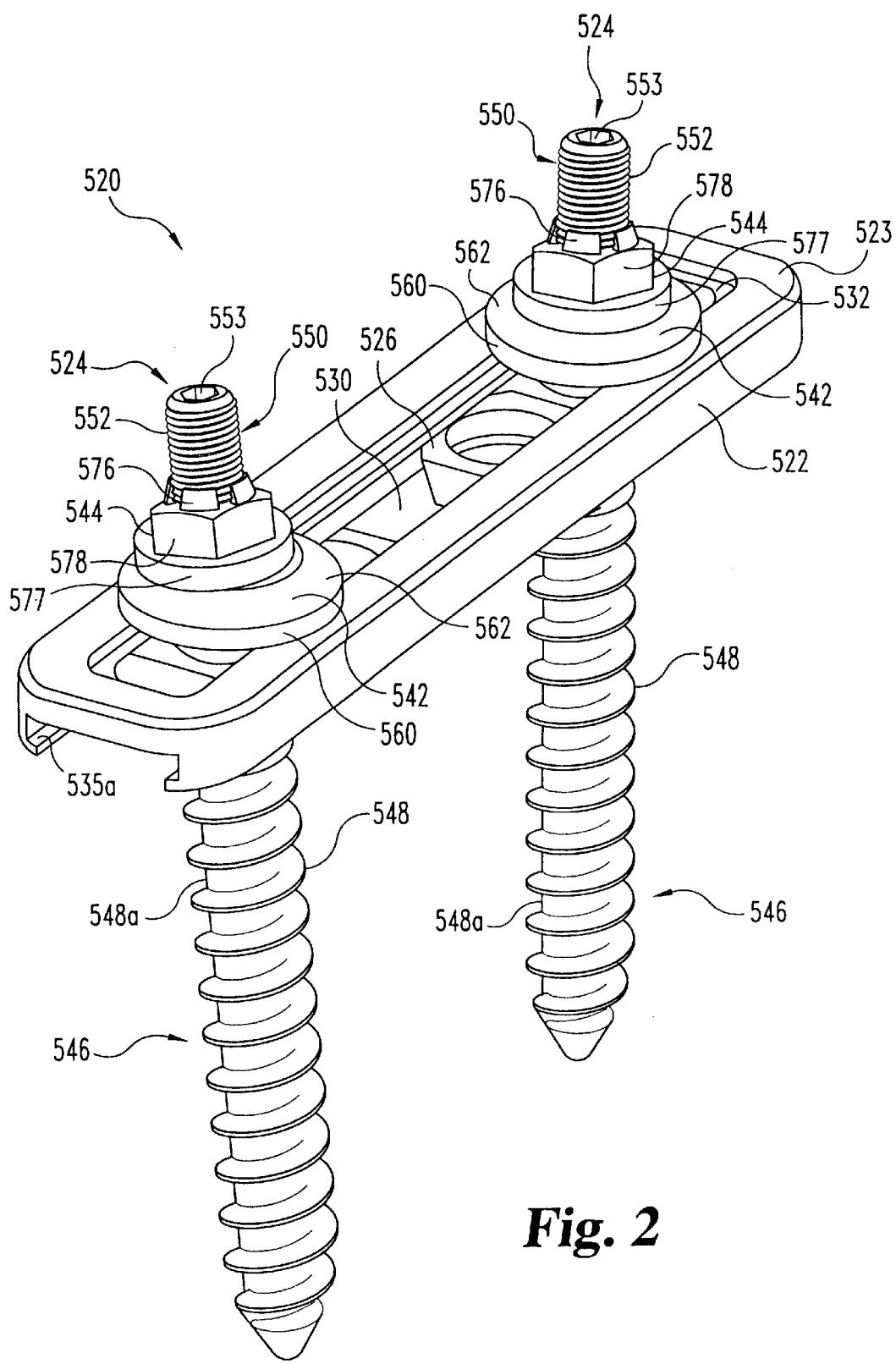
FIG. 2 is a perspective view of one embodiment of the system of the present invention.
Figure 3:
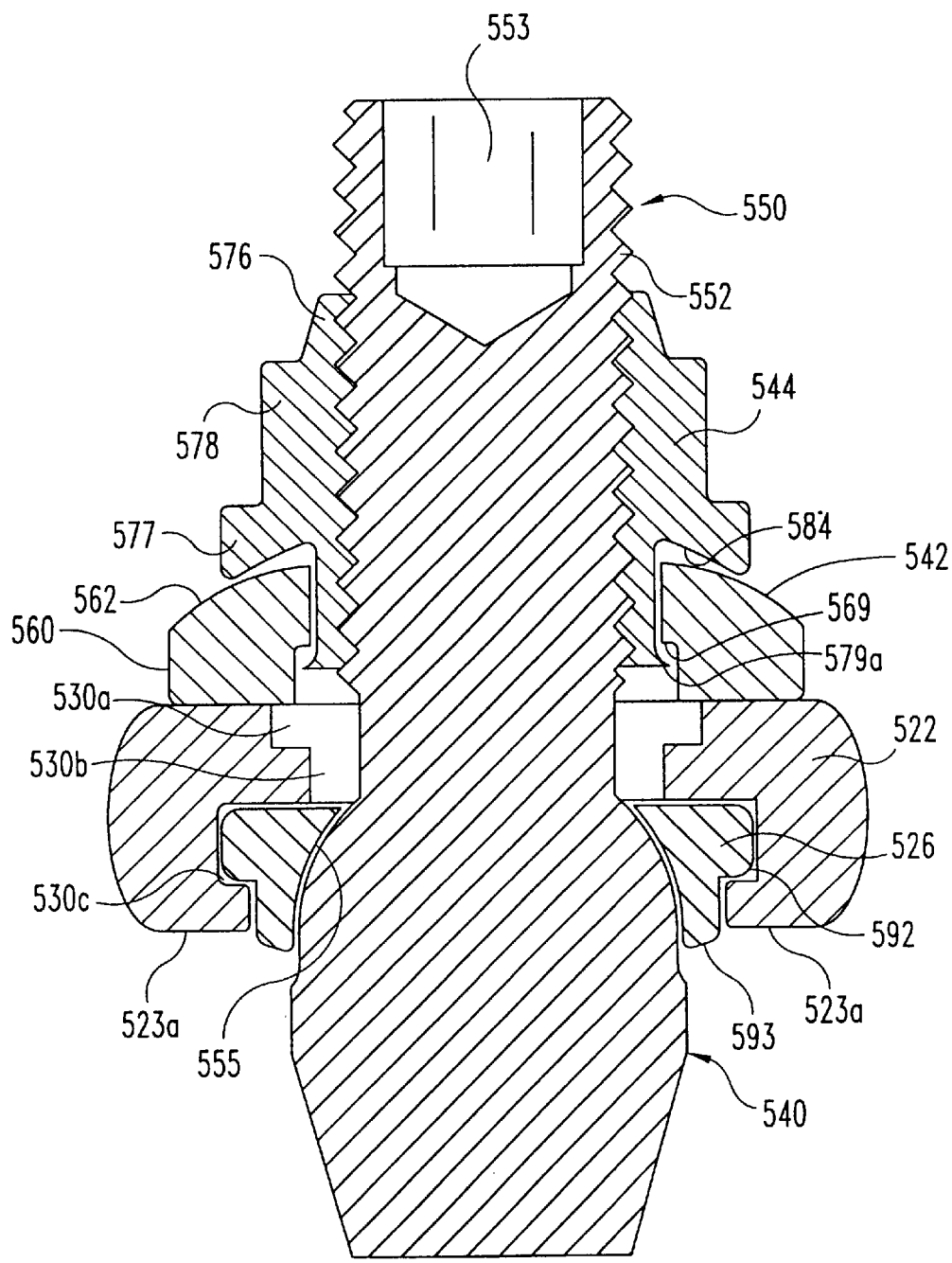
FIG. 3 is a sectional view of the embodiment of the invention illustrated in FIG. 2 taken along line 3—3 in FIG. 2 and viewed in the direction of the arrows.

Referring generally to FIGS. 2–3, one embodiment of the orthopedic implant system 520 of the present invention is illustrated. In that embodiment, implant system 520 includes an elongated member such as a bone plate 522, a pair of bone anchor assemblies 524 and a set of supports or stabilizers 526. Differing numbers of any of these elements may be utilized without departing from the scope of this invention. For example, a plurality of elongated members 522 can be used in conjunction with each other, or a greater or lesser number of bone anchor assemblies 524 may be used, depending upon the configuration of the elongated member, the medical problem to be addressed, and/or any other factors. The present invention contemplates at least one elongated member 522, one bone anchor assembly 524, and one stabilizer 526 for each bone anchor assembly 524.

Figure 4A:
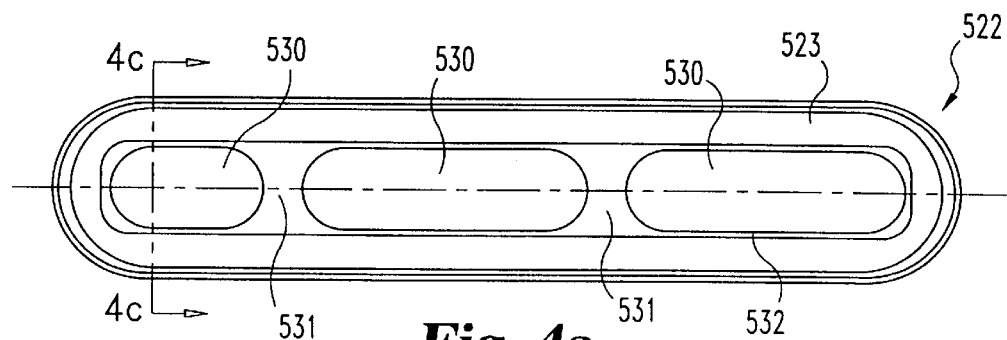
FIG. 4a is a top view of one embodiment of an orthopedic plate used in the present invention.
Figure 4B:
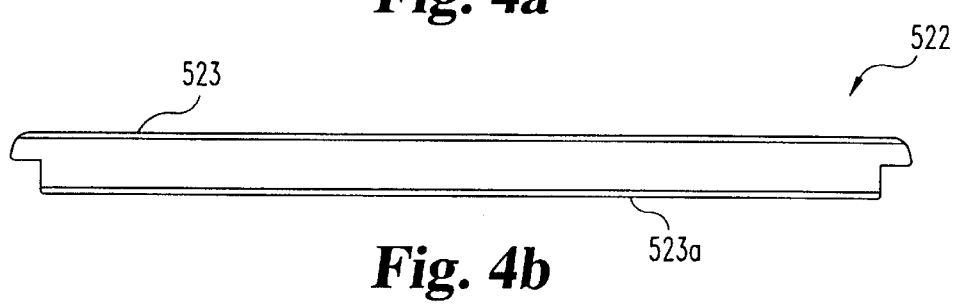
Figure 4C:
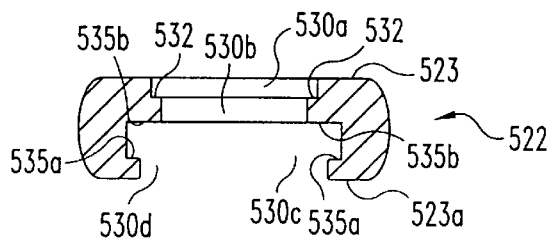
FIG. 4c is a cross-sectional view of the embodiment of the orthopedic plate illustrated in FIG. 4a, taken along the line 4c—4c in FIG. 4a and viewed in the direction of the arrows.

Referring now generally to FIGS. 4a–4c, there is shown an embodiment of bone plate 522. Plate 522 has a generally rounded-rectangular or oval shape, an upper surface 523 and a lower surface 523a. Plate 522 further includes one or more elongated slots 530 therethrough from upper surface 523 to lower surface 523a, which extend along a longitudinal axis of plate 522. Slots 530 have a generally open geometry enabling bone anchor assemblies 524 to be placed at any of an infinite number of positions within slots 530. In the illustrated embodiment, slots 530 within plate 522 have an upper portion 530a adjacent to upper surface 523, a medial portion 530b, a longitudinal channel 530c, and a lower portion 530d adjacent to lower surface 523a of plate 522. Slot portions 530a–530d generally have a non-uniform width (i.e. the horizontal dimension in FIG. 4c). Plate 522 can also include one or more cross members 531 to separate medial portions 530b and create a multiple slot configuration, thereby providing added rigidity and dimensional stability to bone plate 522 without compromising the open geometry, but the upper portion 530a, channel 530c and lower portion 530d are continuous through the longitudinal dimension of plate 522. Upper portion 530a is further partially bounded by ledge 532, and channel 530c is partially bounded by ledge 535a and ceiling surface 535b. Bone plate 522 is of sufficient length to bridge one or more vertebrae 521 for which stabilization is required, as will be appreciated, and various dimensions of the plate and its features, as well as numbers of slots, are within the scope of the present invention.

Figure 4D:
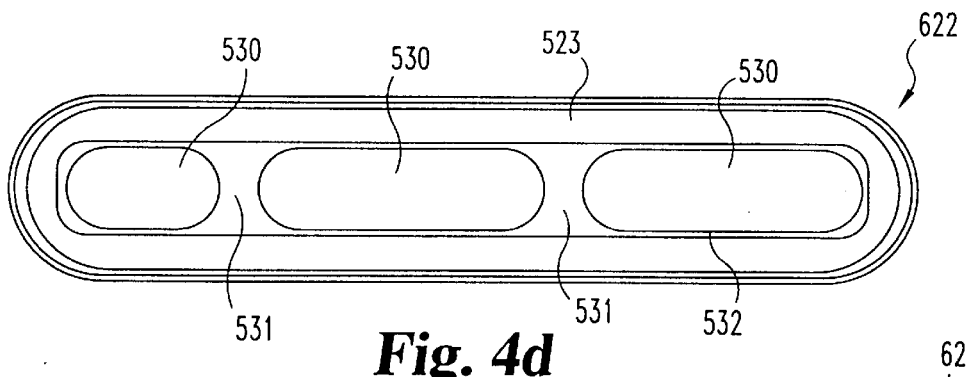
FIG. 4d is a top view of a second embodiment of an orthopedic plate used with the embodiment of the invention illustrated in FIG. 1.
Figure 4E:
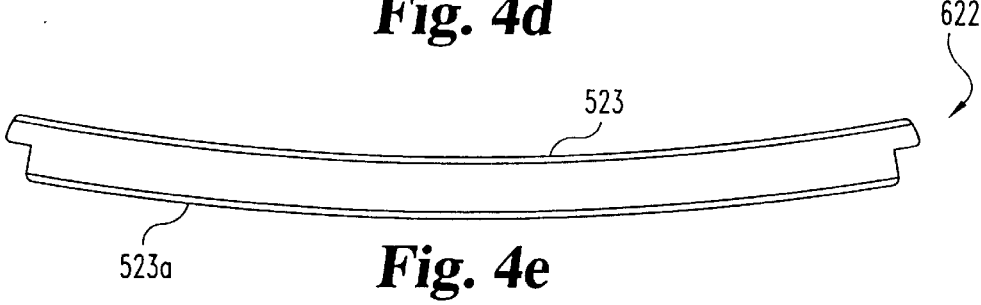
FIG. 4e is a side elevational view of the second embodiment of the orthopedic plate illustrated in FIG. 4d.

FIGS. 4c and 4d illustrate an alternative embodiment of bone plate 622, which is different from plate 522 only insofar as plate 622 and its internal features, including slot portions 530a–530d, are bent or curved. The curved plate 622 offers surgeons added convenience in situation where the bone members 521 have to be retained in an arc, e.g. maintaining the normal lordotic or kyphotic curves of the spine.

Referring now generally to FIGS. 7–10, there is shown an embodiment of a bone anchor assembly 524 of the present invention, which can be used with elongated member 522. Generally, bone anchor assembly 524 includes an anchoring member such as bone bolt 540, an arcuate washer 542, and a nut 544. In the illustrated embodiment, washer 542 and nut 544 are affirmatively coupled so that they cannot be easily separated, yet they are rotatable and translatable with respect to each other.

Figure 7:
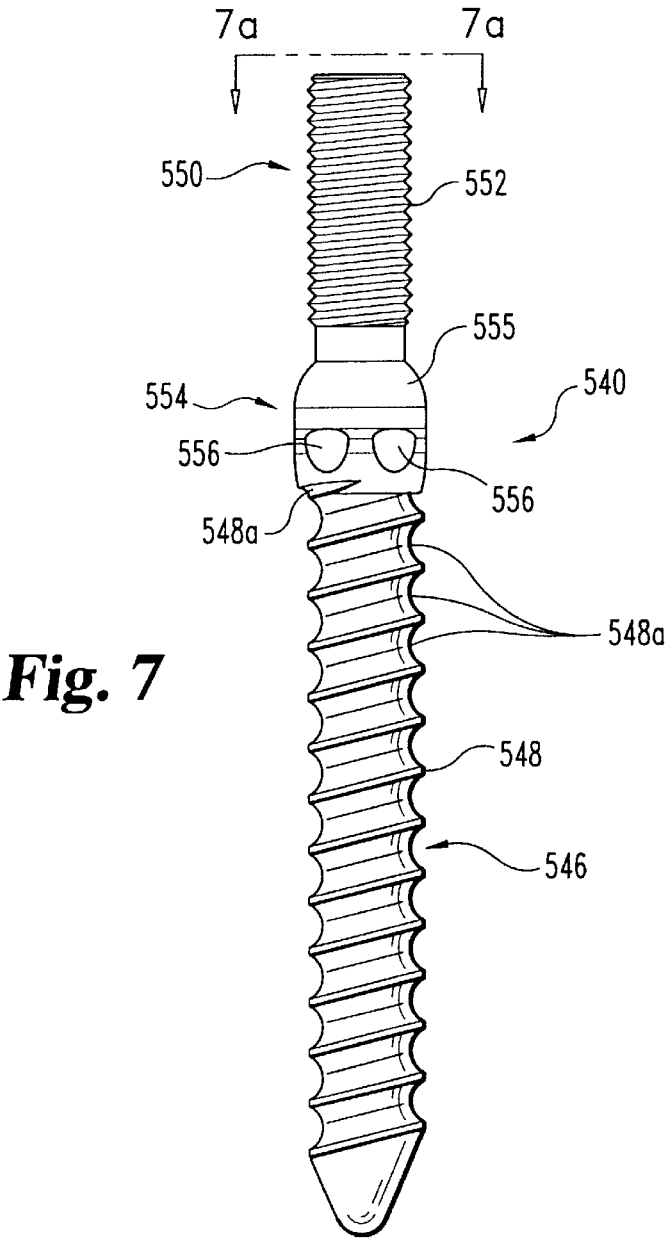
FIG. 7 is a side view of an embodiment of a bone bolt used with the embodiment of the invention illustrated in FIG. 2.
Figure 7A:
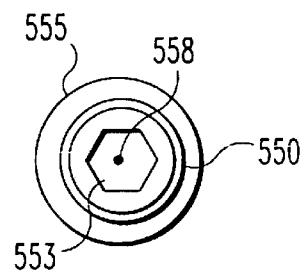

FIGS. 7 and 7a show one embodiment of bone bolt 540, in which bolt 540 includes a bone-engaging portion 546 with a cancellous thread 548, a proximal portion or post 550 having a machine threaded section 552 and a tool engaging recess 553, and an intermediate portion 554. In one particular embodiment, thread 548 adjoins the intermediate portion 554 and root diameter 548a of thread 548 increases in continuous fashion as thread 548 approaches intermediate portion 554, thus providing a substantially smooth junction with intermediate portion 554. Intermediate portion 554 includes a rounded upper section 555 and one or more flattened areas 556, the latter being provided for insertion or removal of bolt 540 with respect to a bone. In the illustrated embodiment, upper section 555 has a spherical configuration, and flattened areas 556 are uniformly spaced in a hexagonal arrangement around the circumference of the intermediate portion 554. Tool-engaging recess 553 is provided for engagement with a tool to enable threading bolt 540 into a bone. Recess 553 may be of any suitable configuration, such as hexagonal or hexalobed, and in the illustrated embodiment, recess 553 is hexagonal. Bolt 540 further includes a cannula 558 through its entire length. Cannula 558 enables bolt 540 to be advanced to the surgical site over a guide wire (not shown), and further allows flow of blood or other bodily fluids through bolt 540, which may provide speedier healing.

Figure 8A:
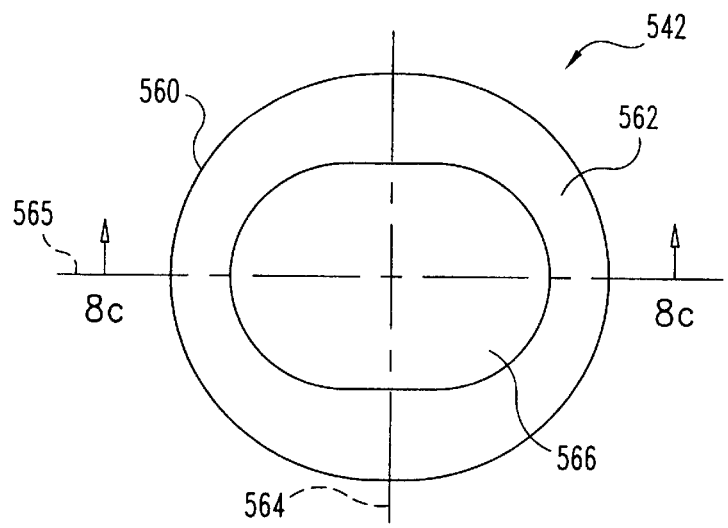
FIG. 8a is a top view of one embodiment of the washer used in the embodiment of the invention illustrated in FIG. 1.
Figure 8B:
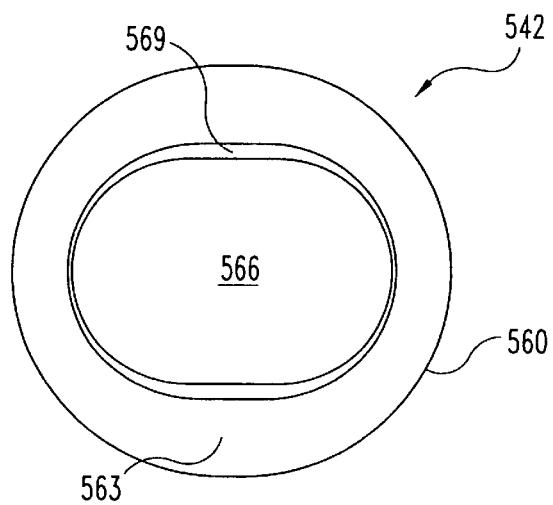
Figure 8C:
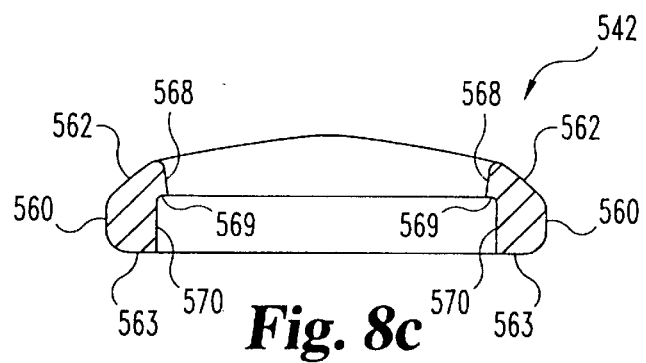
FIG. 8c is a cross-sectional view of the embodiment of the washer illustrated in FIG. 8a, taken along line 8c—8c in FIG. 8a and viewed in the direction of the arrows.

FIGS. 8a and 8b show an embodiment of arcuate washer 542 of the present invention. Washer 542 has a generally cylindrical body 560, a rounded head 562, a substantially flat undersurface 563, and an aperture 566 disposed therethrough. Viewed from the top, aperture 566 is oblong or oval in shape and has a minor axis 564 and a major axis 565. Aperture 566 is bounded by inner wall sections 568 and 570. In the illustrated embodiment, wall section 568 is decreasingly tapered from head 562 toward undersurface 563, and wall section 570 is substantially cylindrical. The diameter of aperture 566 at the lowest portion of wall section 568 is smaller than the diameter of inner wall 570, with the result that the junction of wall sections 568 and 570 form a step or undercut 569. Alternate configurations of wall sections 568 and 570 that form a similar undercut, are also possible. For example, inner walls 568 and 570 may be spherical or conical or a combination thereof.

Figure 9A:
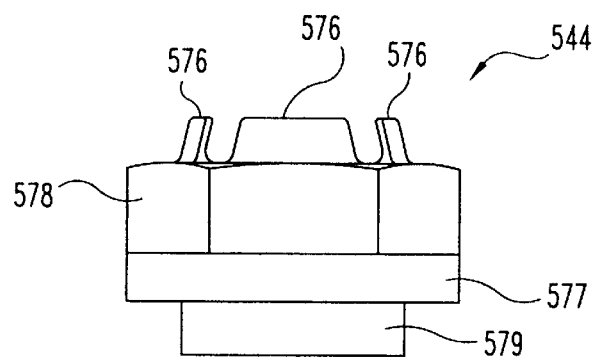
FIG. 9a is a side elevation view of one embodiment of a nut used in the embodiment of the invention illustrated in FIG. 2.
Figure 9B:
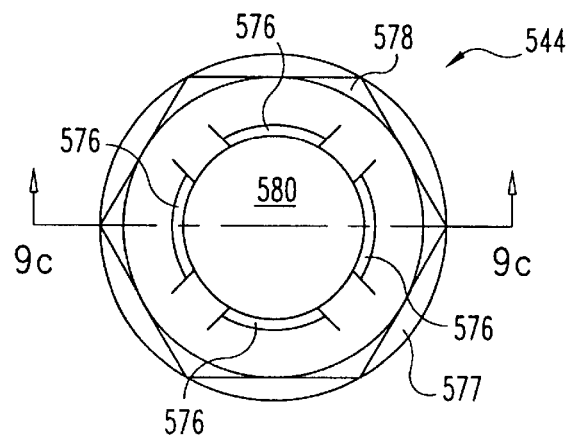
Figure 9C:
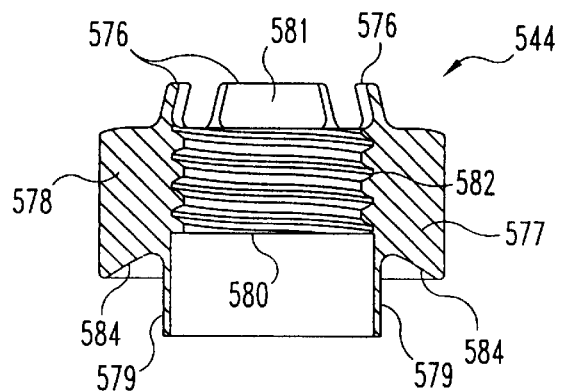
FIG. 9c is a cross-sectional view of the embodiment of the nut illustrated in FIG. 9a, taken along line 9c—9c in FIG. 9b and viewed in the direction of the arrows.

Referring now generally to FIGS. 9a–9c, nut 544 includes tabs 576, a skirt portion 577, a body portion 578, and an downwardly-projecting sleeve portion 579. Nut 544 also includes an aperture 580 extending longitudinally through body portion 578 and sleeve portion 579. Tabs 576 extend upward in an inward incline from body portion 578 and, in the illustrated embodiment, define a passageway 581 that communicates with aperture 580. Body portion 578 includes a conventional outer torque application surface which is capable of being coupled to torque applying tools. In this embodiment, body portion 578 is configured as a hexhead, but any known configuration of the nut portion 578 that will allow application of torque to nut 544 can be used. Aperture 580 is substantially cylindrical with a female thread 582 formed therein. Thread 582 in aperture 580 is configured to threadably receive machine threaded section 552 of post 550. Passageway 581 has a diameter substantially similar to the root diameter of machine-threaded section 552 of bolt 540.

Skirt portion 577, in the illustrated embodiment, is integral with and extends below body portion 578, and is substantially conical in shape, with a substantially conical inner surface 584 extending around sleeve portion 579. It will be appreciated that other geometric shapes could also be used for skirt portion 577 and or inner surface 584. In the illustrated embodiment, sleeve portion 579 extends integrally from approximately the junction of skirt portion 577 and body portion 578 to beyond the lower edge of skirt portion 577. Sleeve portion 579 is adapted to be received in aperture 566 of washer 542, and thus has an outer diameter slightly smaller than minor axis 564 of aperture 566.

In a specific embodiment of the present invention shown in FIGS. 10a–10d, arcuate washer 542 and nut 544 are coupled so that they are rotatable and translatable relative to each other, but are not easily disconnected or uncoupled. The coupling in this embodiment is accomplished by first inserting sleeve portion 579 of nut 544 into aperture 566 of arcuate washer 542 such that the inner surface 584 of skirt portion 577 is proximate to head 562 of arcuate washer 542. A lower part of sleeve portion 579 is swaged or otherwise expanded to form a flared edge 579a around substantially the entire circumference of sleeve portion 579. Sleeve portion 579 can be swaged or expanded by any conventional method. The resultant flared edge 579a has a diameter smaller than that of wall section 570 of washer 542, but larger than that of the smallest portion of wall section 568, so that flared edge 579a is retained within aperture 566 of washer 542 by undercut 569. So coupled, arcuate washer 542 and nut 544 can fully rotate relative to each other, and they can further move translationally along the major axis 565 with respect to each other. As seen most clearly in FIG. 10d, in one embodiment arcuate washer 542 has a top surface that is convex, and nut 544 has a lower surface that is concave, to enhance the connection between them, particularly when nut 544 is toward one end or another of aperture 566 in washer 542.

Coupling washer 542 and nut 544 in this manner reduces the number of components to be handled by the surgeon, thereby increasing ease of use. Additionally, the coupled washer-and-nut component is larger than either separate component, which further improves handling of the implant and lessens the likelihood of dropped, misthreaded, or otherwise misused parts. It will be appreciated that other ways of coupling washer 542 and nut 544 can be used, such as expanding a medial part of sleeve portion 579 rather than an end part, or by providing additional conventional structure for coupling two parts, such as spring-loaded latches or ball-detent structure, clamps or other similar holding structures.

Figure 5A:
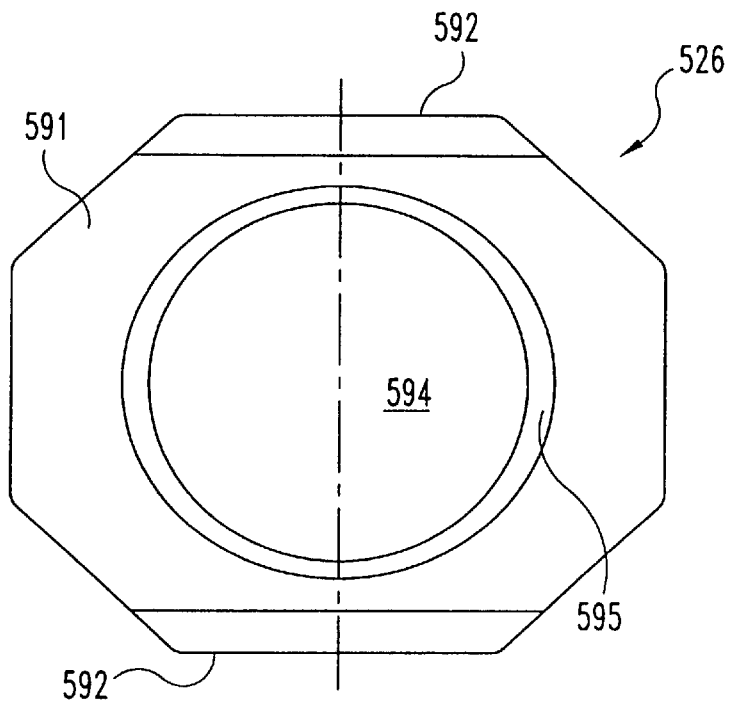
FIG. 5a is a top view of one embodiment of a stabilizer used with the embodiment of the invention illustrated in FIG. 2.
Figure 5B:
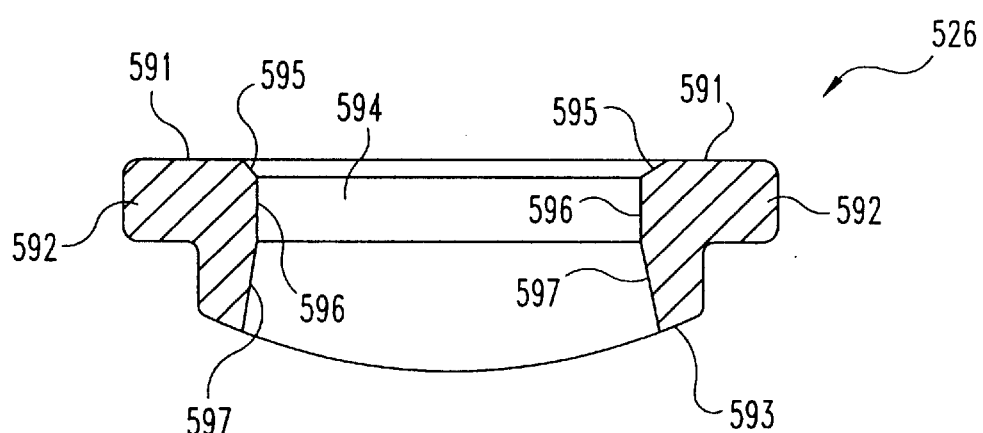
FIG. 5b is a cross-sectional view of the embodiment of the orthopedic stabilizer illustrated in FIG. 5a, taken along the line 5b—5b in FIG. 5a and viewed in the direction of the arrows.
Figure 6:
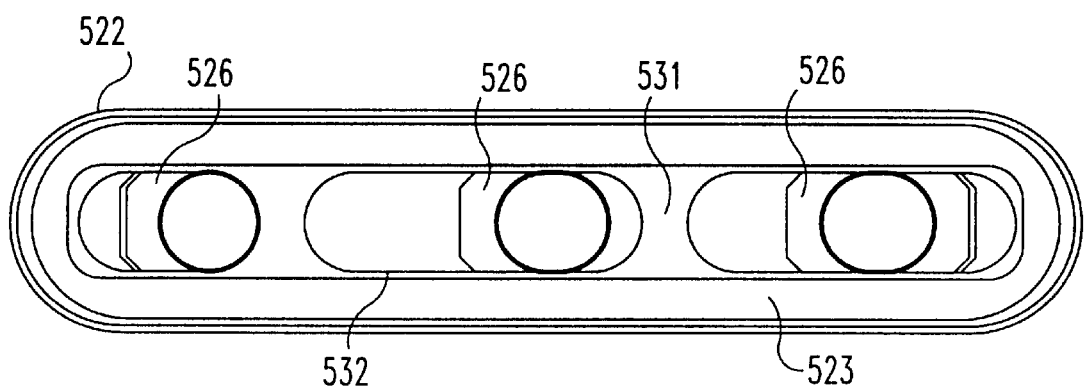
FIG. 6 is a top view of the embodiment of the orthopedic plate illustrated in FIG. 4a, shown with embodiments of the stabilizer illustrated in FIG. 5a fitted therein.

Referring now generally to FIGS. 5a and 5b, implant system 520 includes one or more stabilizers or supports 526. In the illustrated embodiment, stabilizer 526 has an elongated-octagon shape with a substantially flat upper surface 591, laterally-extending finger portions 592 and a rounded lower surface 593. Stabilizer 526 also includes an opening 594 therethrough from upper surface 591 to lower surface 593. Opening 594 is bounded, in a particular embodiment, by a top wall section 595, a medial wall section 596, and a lower wall section 597. In a specific embodiment, top wall section 595 is decreasingly tapered from upper surface 591 toward medial wall section 596, which is substantially cylindrical. Lower wall section 597 is substantially conical so as to receive rounded upper section 555 of bolt 540 and permit multi-axial motion of bolt 540 with respect to stabilizer 526 and plate 522, as further described below.

Other wall configurations are contemplated as being within the scope of the present invention. For example, wall sections 595–597 could form a single conical wall bounding bore 594. Further, other configurations of stabilizer 526 are contemplated as within the scope of the present invention, including those disclosed in U.S. Provisional Applications Ser. Nos. 60/129,587 and 60/149,774, which applications are incorporated by reference herein.

FIG. 1 shows one embodiment of an orthopedic implant 520 of the present invention fixed to a series of vertebrae 521 for stabilizing or restraining vertebrae 521 in a desired positional relationship. In particular, each of the two bone anchor assemblies 524 is optimally aligned to the respective geometry of a bone 521, which may cause assemblies 524 not to be parallel to each other or orthogonal to the bone plate or elongated member 522. The washer 542 and nut 544 of the present invention enables each of the bone screws 540 to be secured to the bone plate 522 regardless of the angular offset from an axis that is substantially normal to a surface of the bone plate. The bone plate 622 as shown is curved in the longitudinal direction for better adaptation to the natural contour of the bone members 521. In other applications, a curved plate may not be necessary. Since plates 522 and 622 are used in substantially the same way, for the sake of clarity the use of the present invention will be described with respect to plate 522.

Referring now generally to FIGS. 1 to 3, one way of assembling and using the illustrated embodiment of implant 520 is as follows. Plate 522 is pre-prepared by placing one or more stabilizers 526 inside plate 522 and within channel 530c, which preparation can occur during or after manufacture of plate 522 and stabilizers 526, or shortly before beginning the implant procedure. Stabilizer 526 is fitted into channel 530c within plate 522 such that finger portions 592 of stabilizer 526 abut ledges 535 and are adjacent to ceiling surface 535b. Referring to FIG. 6a to 6d, one or more stabilizers 526 may be inserted into channel 530c via an open end of plate 522. Stabilizers 526 can be placed at any longitudinal position along channel 530c, so that bolt 540 can be fixed to plate 522 at any longitudinal position along plate 522.

After the surgeon has drilled one or more holes into bone or bones 541, bolt(s) 540 are threaded into the hole(s) via cancellous threads 548 of bone-engaging portion 546, but not to cover flattened areas 556 of bolt 540. Plate 522 with inserted stabilizer(s) 526, is placed over bone bolts 540, so that intermediate portions 554 are within bore 594 of a respective stabilizer 526, and proximal portions 550 extend through the upper surface 523 of plate 522. Plate 522 can then be adjusted both translationally (by moving bolts along slot 530 and associated stabilizer 526 along channel 530c) and multi-axially (by pivoting plate 522 and stabilizer 526 on upper surface 555 of intermediate portion 554) with respect to bolts 540. The rounded upper surfaces 555 of intermediate portions 554 of bone bolts 540 are able to articulate within bore 594 and wall portions 597 and 598 of stabilizers 526, and bone bolts 540 may thereby form any of a variety of angles with respect to plate 522. It will be seen with reference to the embodiment of the invention illustrated in FIG. 3 that lower surface 593 of stabilizer 526 does not approach flattened areas 556 or bone-engaging thread 548 of bolt 540.

When the desired positioning of the vertebrae 541 and the plate 522 with respect to bolts 540 is achieved, a coupled washer 542 and nut 544 are threaded onto proximal portion 550 of each bone bolt 540, so that proximal portion 550 extends through aperture 566 of washer 542 as well as threaded aperture 580 and passageway 581 of nut 544. Since inner wall section 568 of washer 542 is tapered, washer 542 can occupy various angular positions relative to proximal portion 550 of bolt 540 as washer 542 and nut 544 are threaded thereon. As the coupled washer 542 and nut 544 approach plate 522 along proximal portion 550, washer 542 is rotated if necessary with respect to bolt 540 and plate 522 to assume a position with respect to plate 522 such that oblong aperture 566 accommodates the angular off-set between post 550 and elongated member 522. Such a position is achieved when the undersurface 563 of washer 542 rests substantially squarely on upper surface 523 of plate 522 when plate 522 is oriented as desired with respect to bolt 540.

Further tightening of nut 544 causes skirt portion 577 to firmly engage and bear against a portion of head 562, providing secure, tight contact between inner surface 584 of skirt portion 577 and head 562 of washer 542. Such tightening of nut 544 on proximal portion 550 forces intermediate portion 554 of bolt 540 against wall portion 597 of stabilizer 526, and upper surface 591 and finger portions 592 against ceiling surface 535b inside plate 522, securely locking plate 522 to bolt 540.

Tabs 576 of nut 544 may lodge under the machine thread on proximal portion 550 of bolt 540, providing substantial resistance or interference fit against backward rotation or other movement of nut 544. Any part of proximal portion 550 that remains above tabs 576 is broken or cut off or sheared away to minimize irritation to surrounding tissues.

In the above description, embodiments incorporating the washer-nut combination 541 are described. It should be understood that other embodiments incorporating separate arcuate washers 542 and nuts 544 are within the scope of the present invention, as for example the embodiments disclosed in U.S. Provisional Application Ser. Nos. 60/129,587 and 60/149,774, which applications are incorporated by reference into the present disclosure in their entirety. Further, it is contemplated that differing sizes of parts or of apertures within parts are within the scope of the present invention.

The parts of the implant system of the present invention may be made available in kits. Such kits may include, for example, a set of elongated members 522 and 622 of various lengths and having differing numbers or orientations of slots and/or bores. Sets of washers, bolts, screws and nuts and washer-nut combinations as disclosed herein can also be provided. Further, tools such as wrenches and screwdrivers compatible with the parts of the implant system of the present invention may also be included. It will be appreciated that the parts of the present invention should be constructed of biocompatible materials such as stainless steel, titanium, titanium alloys, certain plastics, or other known materials.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A combination for use in medical applications, comprising:
    a washer having an upper surface, a lower surface, and an aperture;
    a fastener having a lower surface to contact said upper surface of said washer, and a sleeve portion that extends into said aperture; and
    a medical implant connected to at least one of said fastener and said washer.

2. The combination of claim 1, wherein said female fastener is a nut having an internally threaded hole.

3. The combination of claim 1, wherein a portion of said sleeve portion has a diameter greater than a dimension of said aperture, whereby said washer and said fastener are movably coupled.

4. The combination of claim 3, wherein said fastener is translationally and rotationally movable with respect to said washer.

5. The combination of claim 3, wherein said aperture of said washer has the form of a slot, whereby said fastener is movable in both translation and rotation with respect to said washer.

6. The combination of claim 1, further comprising a bone fixation device having a threaded upper portion, said upper portion and said fastener being threadedly connected.

7. The combination of claim 6, further comprising an elongated member having a slot, wherein said bone fixation device extends through said slot and said lower surface of said washer contacts said elongated member.

8. The combination of claim 7, further comprising a stabilizer having an opening therethrough, said stabilizer occupying one of an infinite number of positions with respect to said elongated member such that said opening communicates with said slot, wherein said bone fixation device extends through and contacts said stabilizer.

9. The combination of claim 1, wherein said upper surface of said washer is convex.

10. The combination of claim 1, wherein said lower surface of said fastener is concave.

11. The combination of claim 1, wherein said lower surface of said fastener has a configuration substantially complementary to said upper surface of said washer.

12. The combination of claim 1, wherein said fastener includes locking tabs.

13. The combination of claim 1, wherein said aperture of said washer is bounded by a tapered wall.

14. The combination of claim 1, wherein said washer includes an undercut surface adjacent said aperture.

15. The combination of claim 14, wherein a portion of said sleeve is swaged to a size larger than an inner dimension of said undercut surface.

16. A method, comprising the steps of:
    providing the combination of claim 1; and
    coupling said combination to a medical implant.

17. The apparatus of claim 1 wherein said fastener has an internal thread.

18. The combination of claim 1, further comprising an elongated member, wherein said lower surface of said washer contacts said elongated member.

19. An orthopedic implant, comprising:
    a base member having a lower surface, an upper surface, and at least one aperture;
    a stabilizer having an opening, said stabilizer being adjacent said base member in one of an infinite number of positions wherein said opening communicates with at least one of said apertures of said base member;
    a fixation member having a first portion for attachment to a bone, a second portion including threads, and an intermediate diametrally enlarged portion, said fixation member extending through said stabilizer and said base member so that said enlarged portion contacts said stabilizer;
    a washer having a rounded top, said washer being around said second portion of said fixation member; and
    a nut including a sleeve portion extending through said washer, said nut being threaded onto said second threaded part of said fixation member,
    whereby said fixation member, said stabilizer and said base member can be locked relative to each other.

20. The implant of claim 19, further comprising at least one additional stabilizer each having an opening therethrough, said at least one additional stabilizer further having at least one lateral finger abutting said base member, wherein said at least one additional stabilizer is in one of an infinite number of positions such that said opening of said at least one additional stabilizer communicates with an aperture of said medical implant.

21. The implant of claim 20, further comprising at least one additional fixation member each having a first portion for fixing to a bone, a second portion including threads, and an intermediate diametrally enlarged portion, said at least one additional fixation member extending through a corresponding one of said at least one additional stabilizers and said medical implant so that said enlarged portion contacts a portion of said corresponding stabilizer.

22. The implant of claim 19, wherein at least a portion of said stabilizer is between said upper and lower surfaces of said base member.

23. The implant of claim 19, wherein a portion of said sleeve has a diameter greater than a dimension of said aperture, whereby said washer and said nut are movably coupled.

24. The implant of claim 23, wherein said nut is translationally and rotationally movable with respect to said washer.

25. The implant of claim 23, wherein said aperture of said washer has the form of a slot, whereby said nut is movable in both translation and rotation with respect to said washer.

26. The implant of claim 19, wherein said aperture of said washer is bounded by a tapered wall.

27. The implant of claim 19, wherein said washer includes an undercut surface adjacent said aperture.

28. A method, comprising:
    inserting at least one bone fixation member into a bone;
    providing a base member having at least one slot therein and a stabilizer having an aperture;
    placing said base member and said stabilizer over said bone fixation member so that said fixation member extends through said stabilizer and said base member;
    orienting said base member with respect to said fixation member to a desired relative position;
    placing a locking combination over said fixation member, said locking combination including a washer and nut that are movably coupled with respect to each other prior to said placing step; and
    threading said nut onto said fixation member, and tightening said nut whereby said base member and said fixation member are locked with respect to each other.

29. The method of claim 28 further comprising the step of moving said nut with respect to said washer.

30. The method of claim 29, wherein said step of moving said nut with respect to said washer occurs substantially in conjunction with said orienting step.

31. The method of claim 29 wherein said moving step includes relative translational movement between said nut and said washer.

32. A combination for use in medical applications, comprising:
 a first element having a lower surface for contacting a surface of a medical implant;
 a second element rotatably coupled with said first element; and
 a bone engaging device for use with said medical implant,
 wherein said first element and said second element adjoin said bone engaging device so that rotation of said second element engages said second element with said bone engaging device so as to press said surface of said first element against said surface of said medical implant and wherein said first and second elements are rotatably coupled prior to engagement of said second element with said bone engaging device.

33. The combination of claim 32 wherein one of said first and second elements has an aperture and the other has a projection, and said first and second elements are coupled by insertion of said projection within said aperture.

34. The combination of claim 33 wherein said projection is a sleeve.

35. The combination of claim 33 wherein a portion of said projection is larger than said aperture so that said first and second elements are rotatably fastened together.

36. The combination of claim 32 wherein said first element is a washer having an aperture and said second element is a nut, said nut having a lower surface to contact said upper surface of said washer, and a sleeve portion that extends into said aperture, and wherein a portion of said sleeve has a diameter greater than a dimension of said aperture, whereby said washer and said nut are movably coupled.

37. The combination of claim 32, further comprising a medical implant, said lower surface of said first element is for contacting said medical implant, and wherein said bone engaging device includes a threaded bone anchor.

38. The combination of claim 37, wherein said medical implant and said bone engaging device are locked with respect to each other upon sufficient rotation of said second element.

39. The combination of claim 37 wherein said medical implant is an orthopedic plate.

* * * * *